(12) United States Patent
Takeuchi et al.

(10) Patent No.: US 11,288,798 B2
(45) Date of Patent: *Mar. 29, 2022

(54) RECOGNIZING PATHOLOGICAL IMAGES CAPTURED BY ALTERNATE IMAGE CAPTURING DEVICES

(71) Applicant: INTERNATIONAL BUSINESS MACHINES CORPORATION, Armonk, NY (US)

(72) Inventors: Yusuke Takeuchi, Kashiwa (JP); Yoshinori Kabeya, Kawasaki (JP); Hiroki Nakano, Otsu (JP); Issei Ozawa, Tokyo (JP); Sho Yonezawa, Kashiwa (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/117,666

(22) Filed: Dec. 10, 2020

(65) Prior Publication Data

US 2021/0097686 A1    Apr. 1, 2021

Related U.S. Application Data

(63) Continuation of application No. 16/203,226, filed on Nov. 28, 2018, now Pat. No. 10,902,590.

(51) Int. Cl.
*G06T 7/00* (2017.01)
*G16H 30/40* (2018.01)
*G06V 20/69* (2022.01)

(52) U.S. Cl.
CPC .......... *G06T 7/0012* (2013.01); *G06V 20/698* (2022.01); *G16H 30/40* (2018.01); *G06T 2207/20081* (2013.01)

(58) Field of Classification Search
CPC ................................. G06T 7/0012; G06T 7/00
See application file for complete search history.

(56) References Cited

U.S. PATENT DOCUMENTS 9,684,960 B2    6/2017  Buzaglo et al.
2009/0262993 A1* 10/2009  Kotsianti .................. G06T 7/62
                                                              382/128
(Continued)

FOREIGN PATENT DOCUMENTS

EP    WO2018045031    *  3/2018    ............... G06K 9/00
WO    2018045031        3/2018

OTHER PUBLICATIONS

Bejnordi et al., "Stain specific standardization of whole-slide histopathological images", 2015 IEEE Transactions on Medical Imaging, 2015, 12 pages.

(Continued)

*Primary Examiner* — Tuan H Nguyen
(74) *Attorney, Agent, or Firm* — Nicholas Bowman; Andrew D. Wright; Roberts Calderon Safran & Cole, P.C.

(57) ABSTRACT

Systems and methods are provided for recognizing pathological images captured by alternate image capturing devices. In embodiments, a computer-implemented method includes: obtaining, by a computing device, a classifier generated based on a plurality of standardized training pathology images associated with a known classification and generated by a first type of device; receiving, by the computing device, an alternate pathology image captured by a second type of device; standardizing, by the computing device, the alternate pathology image; determining, by the computing device, a classification of the alternate pathology image based on applying the generated classifier; and outputting, by the computing device, information regarding the (Continued)

determined classification to aid in diagnosis of a medical condition represented by the alternate pathology image.

20 Claims, 9 Drawing Sheets

(56) References Cited

U.S. PATENT DOCUMENTS

| | | |
|---|---|---|
| 2013/0301898 A1* | 11/2013 | Jain ................... G06T 7/0012 |
| | | 382/133 |
| 2016/0042511 A1 | 2/2016 | Chukka et al. |
| 2017/0061608 A1 | 3/2017 | Kim et al. |
| 2018/0122068 A1 | 5/2018 | Garnavi et al. |
| 2020/0167910 A1 | 5/2020 | Takeuchi et al. |

OTHER PUBLICATIONS

Ruifrok et al., "Quantification of histochemical staining by color deconvolution", Anal Quant Cytol Histol 23: 291-299, 2001, 21 pages.

Mell et al., "The NIST Definition of Cloud Computing", NIST, Special Publication 800-145, Sep. 2011, 7 pages.

List of IBM Patents or Patent Applications Treated as Related, dated Dec. 10, 2020, 1 page.

* cited by examiner

RECOGNIZING PATHOLOGICAL IMAGES CAPTURED BY ALTERNATE IMAGE CAPTURING DEVICES

BACKGROUND

The present invention generally relates to recognizing pathological images and, more particularly, to recognizing pathological images captured by alternate image capturing devices.

Pathological images, created as Whole Slide Images (WSIs) can be recognized for diagnosing a medical condition. For example, to recognize a WSI, a trained classifier is generated through a deep learning or machine learning process in which the classifier is trained from WSIs of known medical conditions. This classifier is applied to a target WSI to diagnose a medical condition of the target WSI.

Generating a WSI involves digitizing a prepared slide using specialized scanning equipment. However, a scanner that creates a WSI is expensive and can only be installed in a limited number of medical facilities having the space, resources, and experts to operate such a scanner.

Transfer learning is a research problem in machine learning that focuses on storing knowledge gained while solving one problem and applying it to a different but related problem. For example, knowledge gained while learning to recognize cars could apply when trying to recognize trucks.

SUMMARY

In an aspect of the invention, a computer-implemented method includes: obtaining, by a computing device, a classifier generated based on a plurality of standardized training pathology images associated with a known classification and generated by a first type of device; receiving, by the computing device, an alternate pathology image captured by a second type of device; standardizing, by the computing device, the alternate pathology image; determining, by the computing device, a classification of the alternate pathology image based on applying the generated classifier; and outputting, by the computing device, information regarding the determined classification to aid in diagnosis of a medical condition represented by the alternate pathology image. In embodiments, the obtaining the classifier comprises: receiving, by the computing device, a plurality of training pathology images associated with the known classification and generated by the first type of device; standardizing, by the computing device, the plurality of training pathology images to produce the standardized training images; and generating, by the computing device, the classifier based on the standardized training images. Advantageously, such methods enable pathology images from image devices other than relatively costly WSI scanners to be classified for use in diagnosing medical conditions with a high degree of accuracy.

In a further aspect, the classifier is associated with attributes and patterns of the standardized plurality of training pathology identifying the known classification and is further generated based on deep machine learning. In a further aspect, the determining the classification of the alternate pathology image is further based on transfer learning using the classifier. Thus, aspects of the invention enable knowledge gained through WSI images to be leveraged for images from non-WSI scanners, thus saving facility and financial resources and enabling more widespread access to pathology classifications.

In an aspect of the invention, there is a computer program product having a computer readable storage medium having program instructions embodied therewith. The program instructions are executable by a computing device to cause the computing device to: obtain a classifier generated based on a plurality of standardized training pathology images associated with a known classification and generated by a first type of device; receive an alternate pathology image captured by a second type of device; standardize the alternate pathology image by applying, to the alternate pathology image, the color correction applied to the plurality of training pathology images; determine a classification of the alternate pathology image based on applying the generated classifier; and output information regarding the determined classification to aid in diagnosis of a medical condition represented by the alternate pathology image. In embodiments, the obtaining the classifier comprises: receiving a plurality of training pathology images associated with the known classification and generated by the first type of device; standardizing the plurality of training pathology images by applying color correction to the plurality of training pathology images to produce standardized training images; and generating the classifier based on the standardized training images. Thus, computer-program products of embodiments of the present invention enable pathology images from disparate devices to be classified for use in diagnosing medical conditions with a high degree of accuracy.

In a further aspect, the determining the classification of the alternate pathology image is further based on transfer learning using the classifier. In a further aspect, the plurality of training pathology images are generated by a whole slide image (WSI) scanner. Thus, embodiments of the invention enable data garnered from relatively expensive WSI images to be leveraged for use with pathology images from other less expensive image capturing devices.

In an aspect of the invention, a system includes: a processor, a computer readable memory and a computer readable storage medium associated with a computing device; program instructions to receive a plurality of training pathology images associated with a known classification and generated by a first type of device; program instructions to standardize the plurality of training pathology images by applying color correction to the plurality of training pathology images and blurring the plurality of training pathology images to produce standardized training images; program instructions to generate and store a classifier associated with attributes and patterns of the standardized training images identifying the known classification; program instructions to receive an alternate pathology image captured by a second type of device; program instructions to standardize the alternate pathology image by applying, to the alternate pathology image to form a standardized alternate pathology image, the color correction as applied to the plurality of training pathology images; program instructions to determine a classification of the alternate pathology image based on comparing attributes and patterns of the standardized alternate pathology image with the attributes and patterns of the standardized training images as identified by the classifier; and program instructions to output information regarding the determined classification to aid in diagnosis of a medical condition represented by the alternate pathology image. The program instructions are stored on the computer readable storage medium for execution by the processor via the computer readable memory. Advantageously, such systems enable pathology images from disparate devices to be classified for use in diagnosing medical conditions.

In a further aspect, the program instructions to determine the classification of the alternate pathology image comprise an instruction to determine the classification based on transfer learning using the classifier. In a further aspect, the first type of device is a WSI scanner and the second type of device is a smartphone; a consumer grade camera; or a commercial-off-the-shelf camera. Thus, embodiments of the invention enable data garnered from relatively expensive WSI images to be leveraged for use with pathology images from other less expensive image capturing devices.

In an aspect of the invention, a computer-implemented method includes: receiving, by a computing device, a plurality of training pathology images associated with a known classification and generated by a first type of device; standardizing, by the computing device, the plurality of training pathology images by applying color correction to the plurality of training pathology images to produce standardized training images; generating, by the computing device, a classifier associated with attributes and patterns of the standardized training images identifying the known classification; receiving, by the computing device, an alternate pathology image captured by a second type of device; standardizing, by the computing device, the alternate pathology image by applying, to the alternate pathology image to form a standardized alternate pathology image, the color correction as applied to the plurality of training pathology images; determining, by the computing device, a classification of the alternate pathology image based on comparing attributes and patterns of the standardized alternate pathology image with the attributes and patterns of the standardized training images as identified by the classifier; and outputting, by the computing device, information regarding the determined classification to aid in diagnosis of a medical condition represented by the alternate pathology image. Advantageously, such methods enable pathology images from different types of imaging devices to be classified for use in diagnosing medical conditions.

In a further aspect, the determining the classification of the alternate pathology image is further based on transfer learning using the classifier. In a further aspect, the applying the color correction includes: converting into a hue, saturation, density (HSD) color space for separation; clustering pixels in the HSD color space; and converting into L*a*b color space based on the clustered pixels. Thus, embodiments of the invention enable data garnered from relatively expensive WSI images to be leveraged for use with pathology images from other less expensive image capturing devices.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

Figure 1:
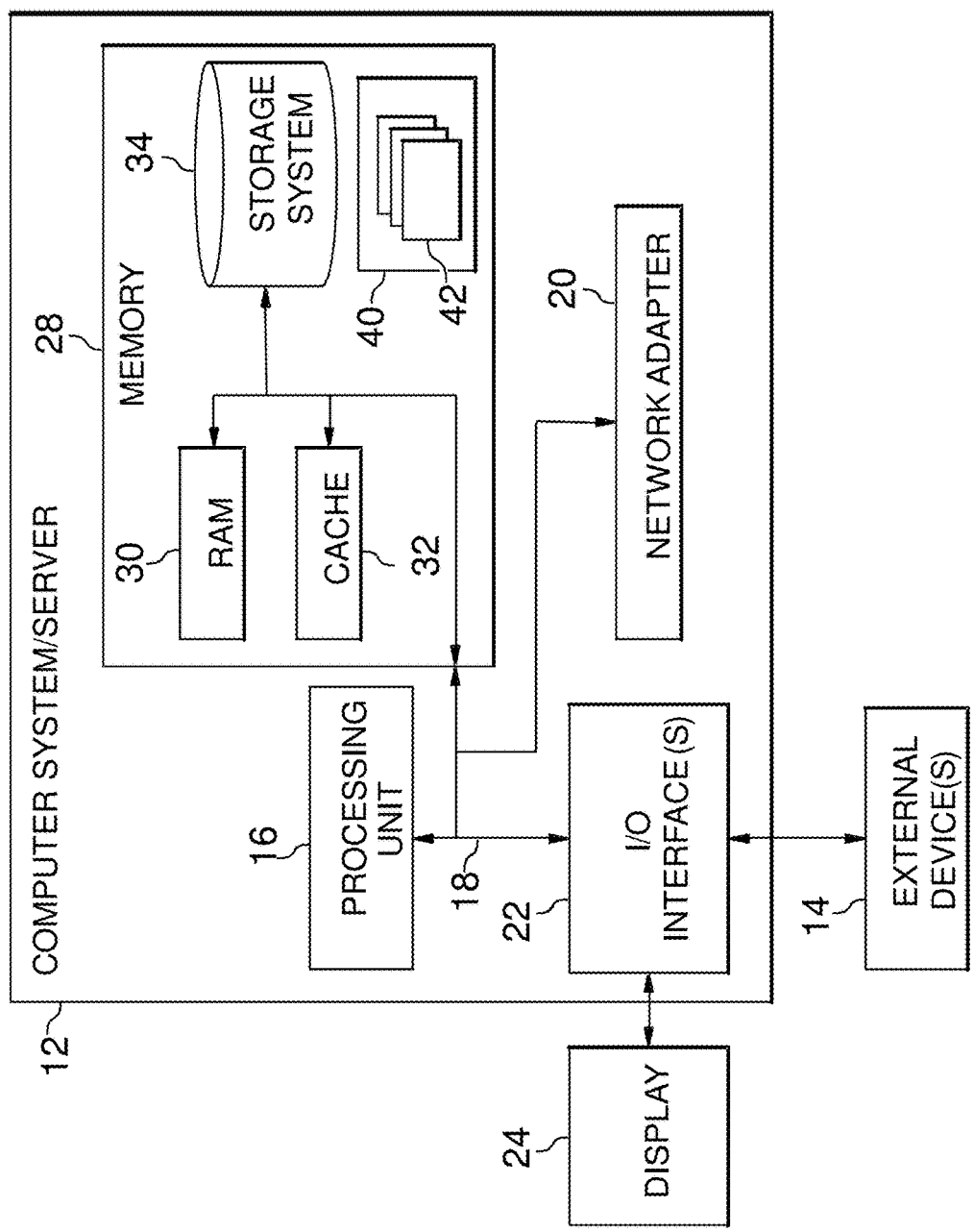
FIG. 1 depicts a cloud computing node according to an embodiment of the present invention.

The present invention generally relates to recognizing pathological images and, more particularly, to recognizing pathological images captured by alternate image capturing devices. Generating a whole slide image (WSI) involves digitizing a prepared slide using specialized scanning equipment. A scanner that creates a WSI is expensive and can only be installed in a limited number of medical facilities having the space, resources, and experts to operate such a scanner. Also, a classifier configured based on WSIs is not capable of being used to recognize, with acceptable accuracy, pathology images captured by devices other than by WSI scanners. However, unlike alternative imaging devices (e.g., charge-coupled devices (CCDs), smartphones, etc.) WSI scanners have the advantage of being able to capture a large number of pathological images. Advantageously, embodiments of the invention leverage the large number of WSI images for training purposes, which enables identification of images captured by other devices.

Accordingly, aspects of the present invention apply color correction and standardization to WSI training images to generate a trained classifier that is applied to pathology images captured by less expensive and more accessible alternate image capturing devices (e.g., smartphones, consumer-grade cameras, commercial-of-the-shelf (COTS) cameras, etc.). In accordance with aspects of the present invention, a medical diagnosis is made by recognizing alternate pathology images (e.g., pathology images captured by an alternate image capturing device) by applying transfer learning using the trained classifier. In this way, it is possible to capture pathology images with a relatively inexpensive alternate image capturing device, and accurately recognize the pathology image (e.g., classify and diagnose a medical condition represented by the pathology image). As a result, substantial facility and financial resources are saved, and a greater number of doctors and other medical professionals will be able to leverage pathology classification technology without the need for expensive WSI scanners.

In embodiments, aspects of the present invention apply deep machine learning techniques to train classifiers to be used to recognize and classify pathology images captured by alternate image capturing devices. In embodiments, WSI training images of a known classification/diagnosis are color corrected and standardized as part of the generation of the trained classifiers for that classification/diagnosis. Different classifiers are trained and generated for different classifications and diagnoses. In embodiments, generating trained classifiers is implemented as a cloud-based service in which WSI training images are provided to a cloud server. Further, once the classifiers are trained, the cloud-based server receives pathology images from alternate image capturing devices, and applies transfer learning and the trained classifier to classify the pathology images.

Aspects of the present invention provide a technical solution to the technical problem of computer-based recognition/classification of pathology images captured by devices other than by WSI scanners. Aspects of the present invention incorporate technical solutions, such as color correction standardization of WSI training images to generate a trained classifier that is used, along with transfer learning, to recognize pathology images captured by devices other than by WSI scanners (e.g., alternate image capturing devices). Aspects of the present invention generate new data (e.g., a newly trained classifier), and use this new data to recognize pathology images captured by alternate image capturing devices. Aspects of the present invention improve the functioning of computer systems by incorporating functions in the computer systems that were not previously possible.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
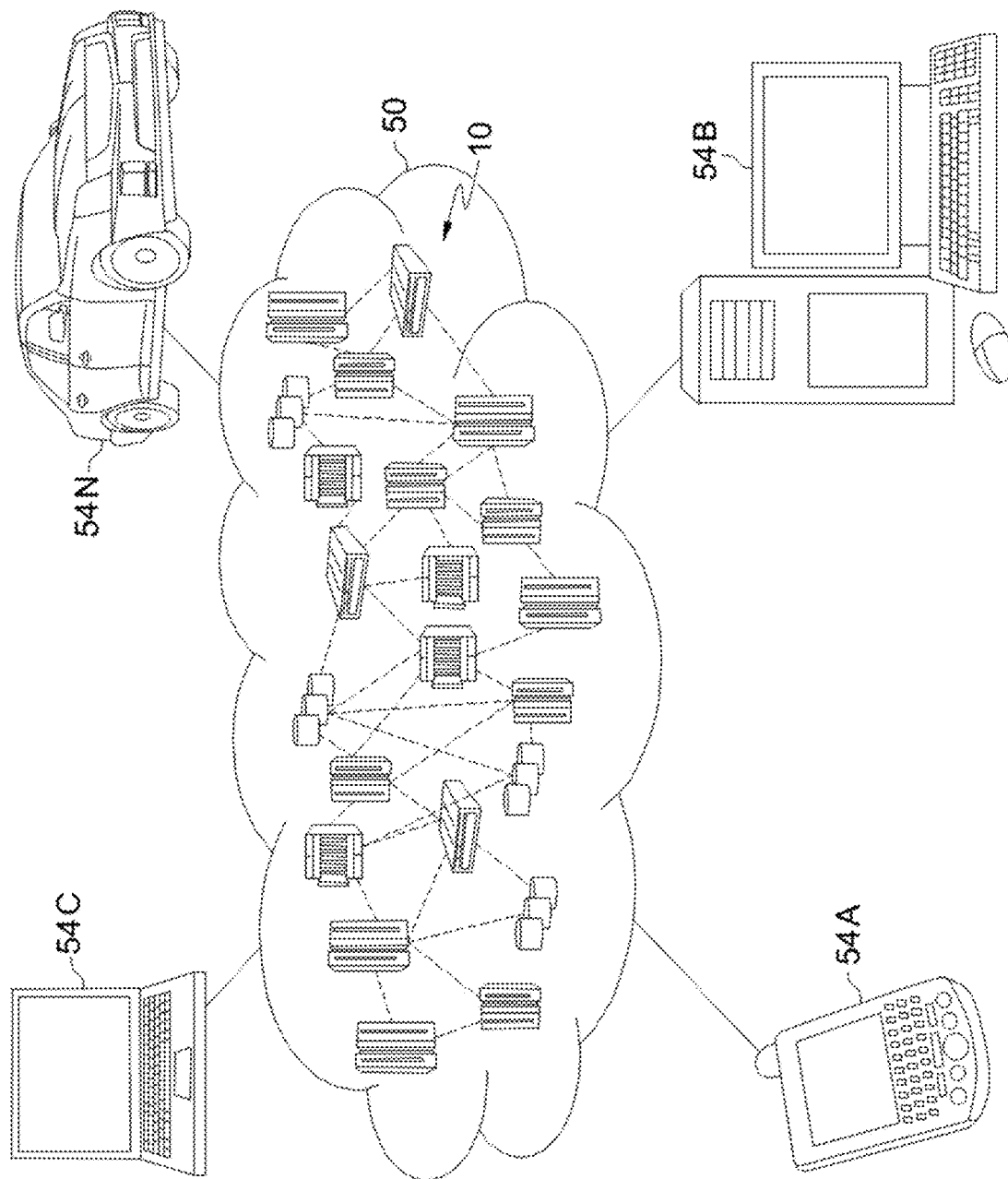
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
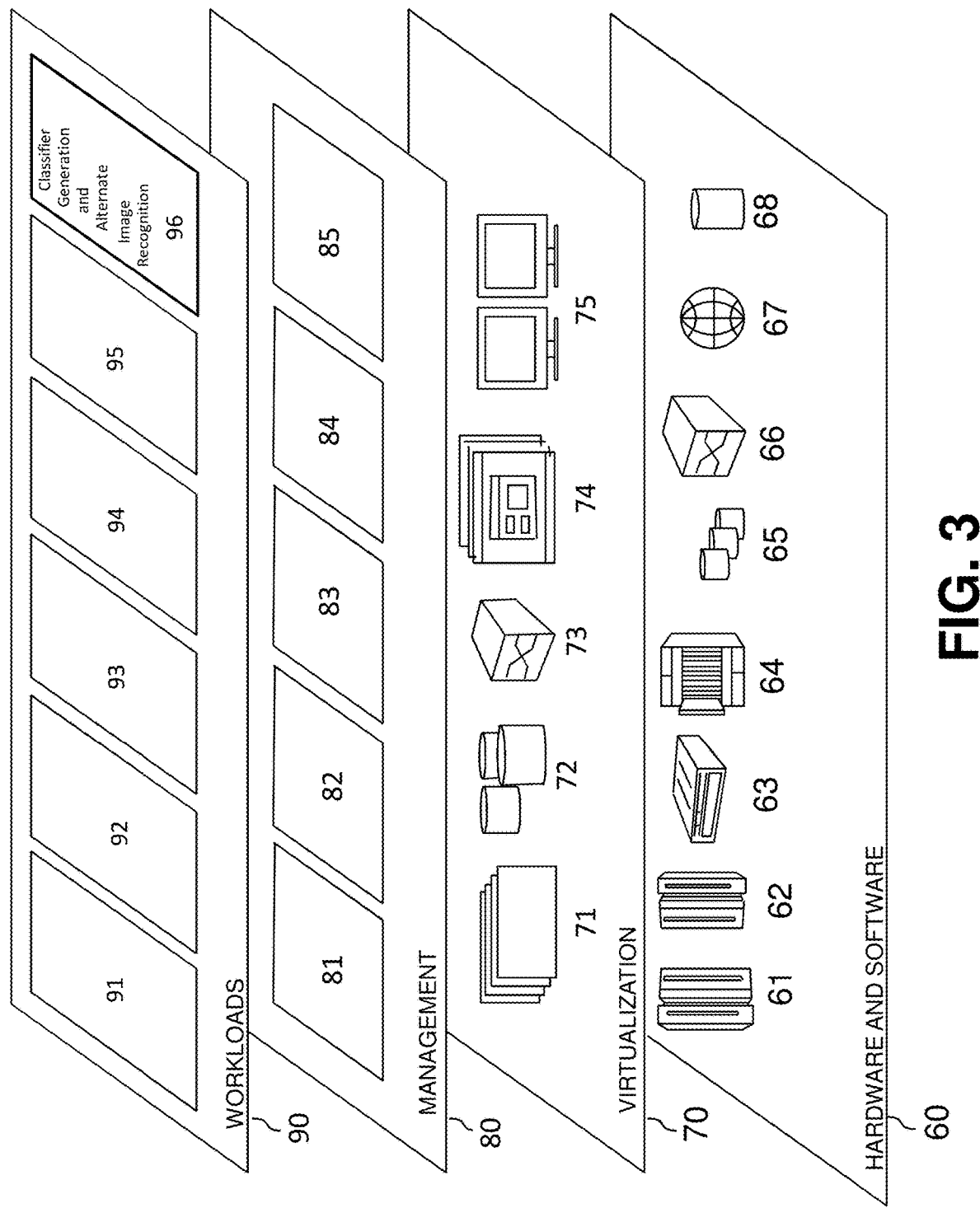
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and classifier generation and alternate image recognition 96.

Referring back to FIG. 1, the program/utility 40 may include one or more program modules 42 that generally carry out the functions and/or methodologies of embodiments of the invention as described herein (e.g., such as the functionality provided by classifier generation and alternate image recognition 96). Specifically, the program modules 42 may receive WSI training images of known classifications, standardize the WSI training images, generate a trained classifier based on the standardize WSI training images, receive an alternate pathology image from an alternate image capturing device, standardize the alternate pathology image, and classify the alternate pathology image using the trained classifier and transfer learning. Other functionalities of the program modules 42 are described further herein such that the program modules 42 are not limited to the functions described above. Moreover, it is noted that some of the modules 42 can be implemented within the infrastructure shown in FIGS. 1-3. For example, the modules 42 may be representative of a pathology image training and recognition device as shown in FIG. 4.

Figure 4:
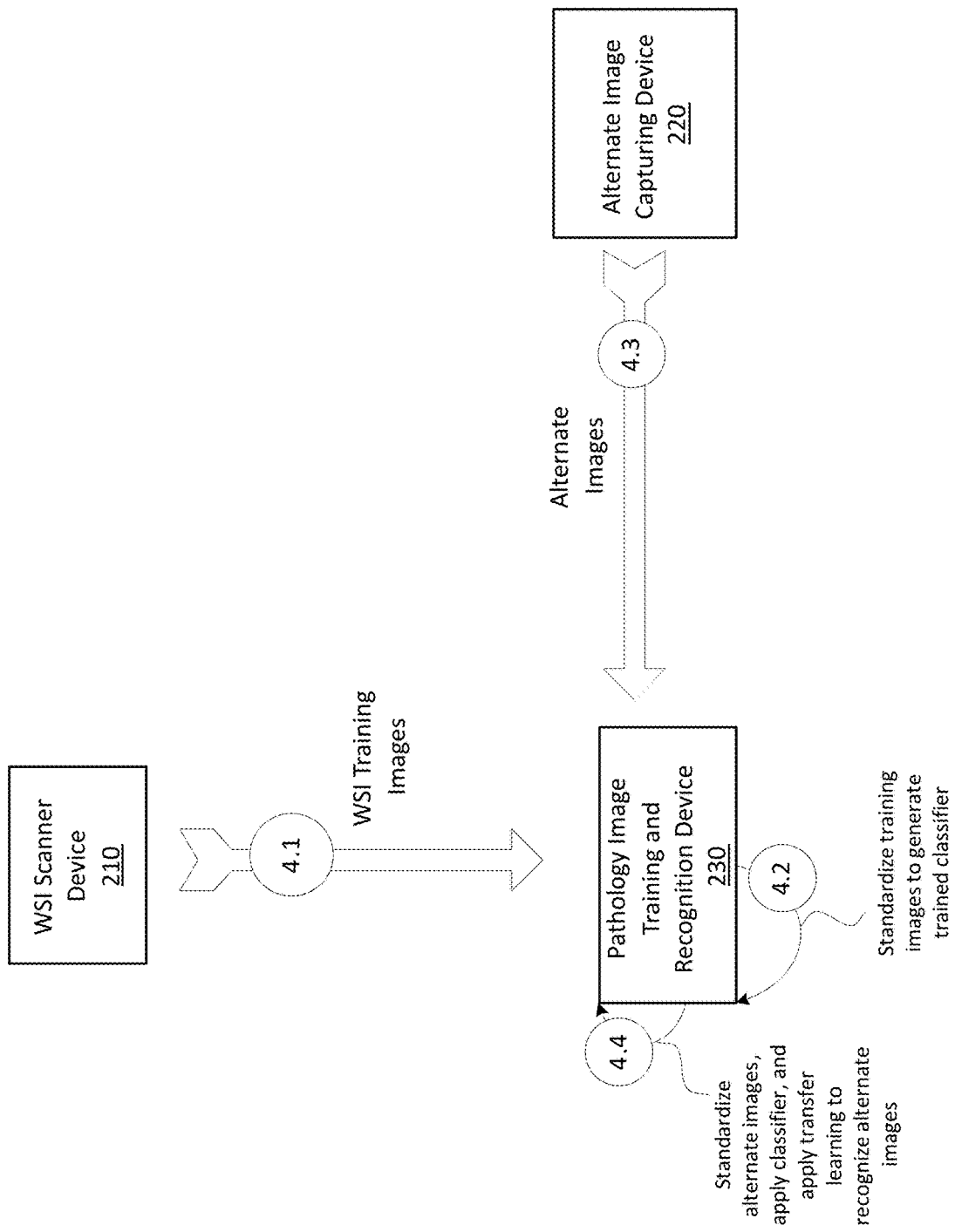
FIG. 4 shows an overview of an example implementation in accordance with aspects of the present invention.

FIG. 4 shows an overview of an example implementation in accordance with aspects of the present invention. In embodiments, the system obtains a classifier generated based on a plurality of standardized training pathology images associated with a known classification and generated by a first type of device, wherein the obtaining the classifier comprises: receiving a plurality of training pathology images associated with the known classification and generated by the first type of device; standardizing the plurality of training pathology images to produce the standardized training images; and generating the classifier based on the standardized training images. In an exemplary embodiment, as shown in FIG. 4, a pathology image training and recognition device 230 receives WSI training images from a WSI scanner device 210 (step 4.1). For example, the pathology image training and recognition device 230 receives WSIs representing a known classification or medical diagnosis. At step 4.2, the pathology image training and recognition device 230 standardizes the training images (e.g., by applying color correction, image blurring, etc.). In embodiments, the standardization is performed in order for the training images to be converted to more closely resemble how those same training images would look if they were captured by an alternate image capturing device 220 (e.g., a smartphone, consumer-grade camera, COTS camera, etc.). In embodiments, the pathology image training and recognition device 230 receives any number of WSIs to standardize and generate a classifier. For example, the pathology image training and recognition device 230 generates the classifier based on potentially tens of thousands of learning images cropped from hundreds of WSIs (e.g., cropped at locations having patterns indicating a medical diagnosis or medical condition). Further, hundreds of thousands of image patches within each cropped image are potentially used to configure and generate the classifier by deep machine learning. In some embodiments, the steps of the obtaining (e.g., the receiving, the standardizing, and the generating) are performed by a single computer device. In other embodiments, the steps of the obtaining (e.g., the receiving, the standardizing, and the generating) are performed by plural different computer devices.

At step 4.3, the pathology image training and recognition device 230 receives alternate images captured by the alternate image capturing device 220. As described herein, the alternate images include pathology images captured by the alternate image capturing device 220 and not by a WSI scanner device (e.g., WSI scanner device 210). At step 4.4, the pathology image training and recognition device 230 standardizes the alternate images (e.g., by applying similar color corrections as was applied to the WSI training images). Further, the pathology image training and recognition device 230 applies the classifier (e.g., generated at step 4.2) and applies transfer learning using the classifier to recognize/classify the alternate images. In embodiments, the accuracy of the evaluated alternate images is approximately 80% when using the classifier from step 4.2 (e.g., in relation to an accuracy of 38% when using a classifier designed to classify WSI images, or an accuracy of approximately 65% when images are analyzed and classified by a pathologist). As a result, pathology images can be more easily captured by relatively low-cost alternate image capturing devices 220 (in relation to using a WSI scanner device 210) and the pathology images are evaluated with a high degree of accuracy.

Figure 5:
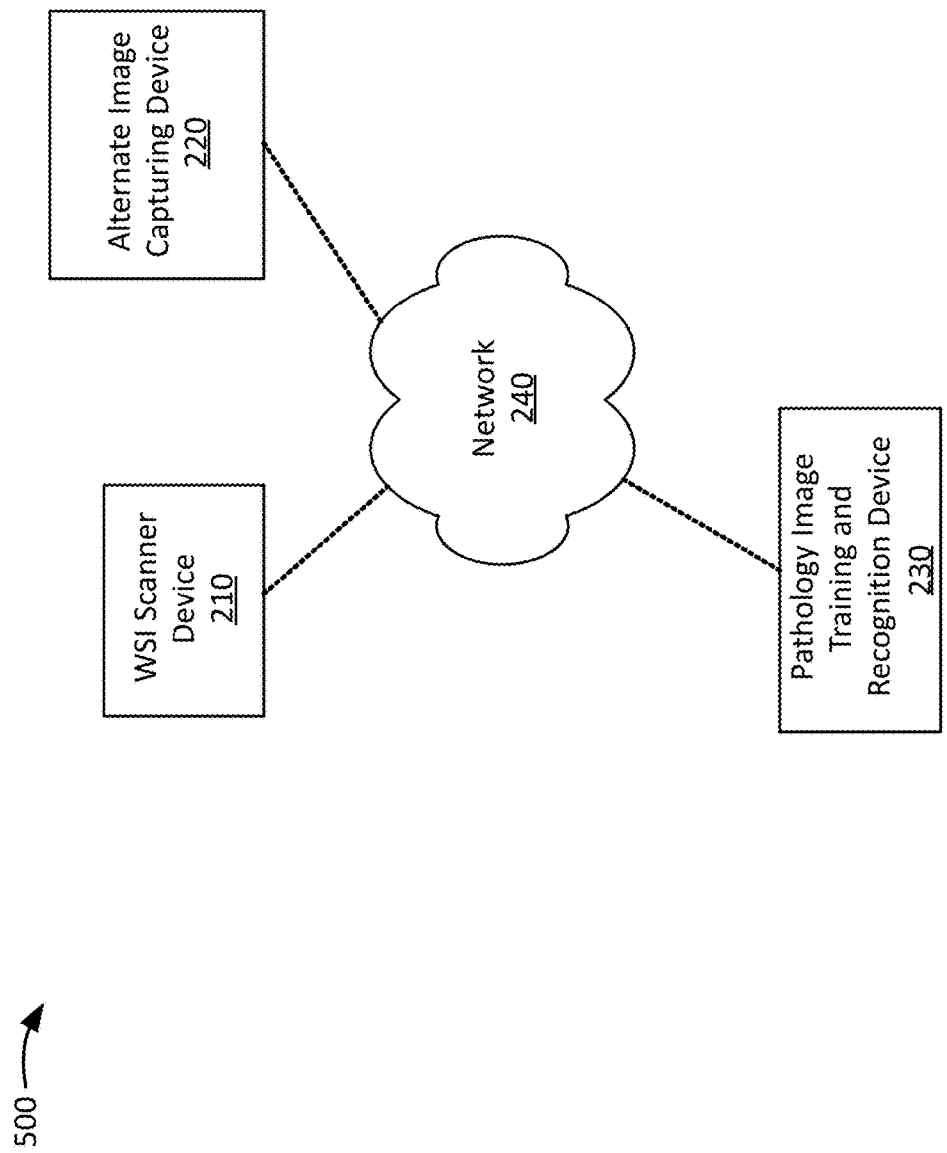
FIG. 5 shows an example environment in accordance with aspects of the present invention.

FIG. 5 shows an example environment in accordance with aspects of the present invention. As shown in FIG. 5, an environment 500 includes a WSI scanner device 210, an alternate image capturing device 220, a pathology image training and recognition device 230, and a network 240. In embodiments, one or more components in the environment 500 may correspond to one or more components in the cloud computing environment of FIG. 2. In embodiments, one or more components in the environment 500 may include the components of computer system/server 12 of FIG. 1.

The WSI scanner device 210 includes a scanning device for generating WSIs of pathology samples. As described herein, the WSI provides training images to the pathology image training and recognition device 230.

The alternate image capturing device 220 includes one or more camera devices that are used to capture a pathology image. In embodiments, the alternate image capturing device 220 includes a smartphone, COTS camera, consumer-grade camera, or the like. In embodiments, the alternate image capturing device 220 includes customized hardware, attachments, adapters, brackets, mounts, lens fittings, or the like that are designed to mount the alternate image capturing device 220 to laboratory equipment (such as microscopes) in order for the alternate image capturing device 220 to capture a pathology image of a sample.

The pathology image training and recognition device 230 includes one or more computing devices (e.g., such as the computer system/server 12 of FIG. 1). As described herein, the pathology image training and recognition device 230 receives WSI training images of known classifications (e.g., from the WSI scanner device 210), standardizes the WSI training images, generates a trained classifier based on the standardized WSI training images, receives an alternate pathology image from an alternate image capturing device 220, standardizes the alternate pathology image, and classifies the alternate pathology image using the trained classifier and transfer learning.

The network 240 may include network nodes, such as network nodes 10 of FIG. 2. Additionally, or alternatively, the network 240 may include one or more wired and/or wireless networks. For example, the network 240 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 240 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks.

The quantity of devices and/or networks in the environment 500 is not limited to what is shown in FIG. 5. In practice, the environment 500 may include additional devices and/or networks; fewer devices and/or networks; different devices and/or networks; or differently arranged devices and/or networks than illustrated in FIG. 5. Also, in some implementations, one or more of the devices of the environment 500 may perform one or more functions described as being performed by another one or more of the devices of the environment 500. For example, in embodiments, the functions described with respect to the pathology image training and recognition device 230 may be performed separately by various combinations of computer devices. Devices of the environment 500 may interconnect via wired connections, wireless connections, or a combination of wired and wireless connections.

Figure 6:
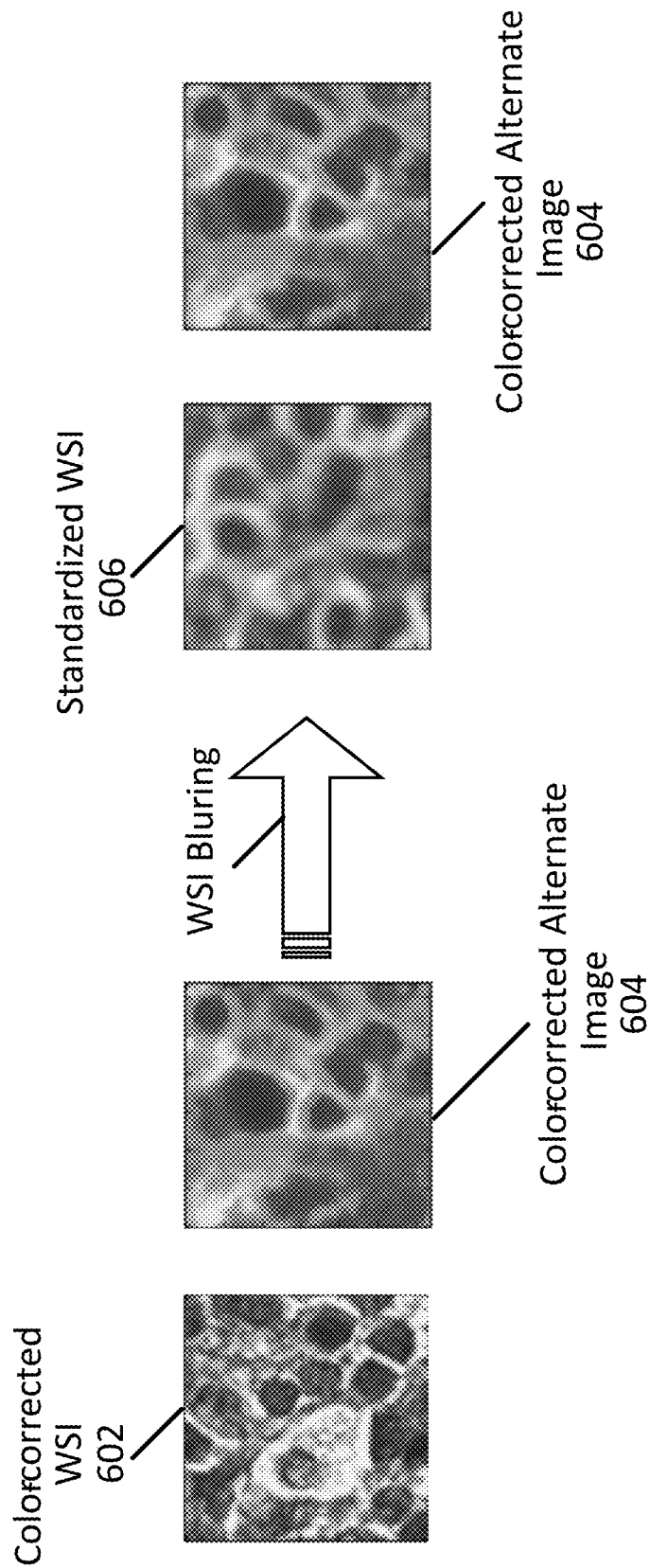
FIG. 6 shows an example implementation of standardizing WSIs and alternate images in accordance with aspects of the present invention.

FIG. 6 shows an example implementation of standardizing WSIs and alternate images. As described herein, the pathology image training and recognition device 230 applies color correction to WSI training images. An example of a color-corrected WSI 602 is shown in FIG. 6. As further described herein, the pathology image training and recognition device 230 applies color correction to alternate images, an example of which is shown in FIG. 6 (e.g., color-corrected alternate image 604). Further, the pathology image training and recognition device 230 applies blurring to the color-corrected WSI 602 to produce a standardized WSI 606 that more closely resembles the color-corrected alternate image 604. In this way, a classifier is produced from the standardized WSI 606 such that the color-corrected alternate image 604 (e.g., a standardized alternate image) can be evaluated using the classifier and transfer learning. Additional details regarding the color correction and blurring is described in greater detail with respect to FIGS. 8 and 9.

Figure 7:
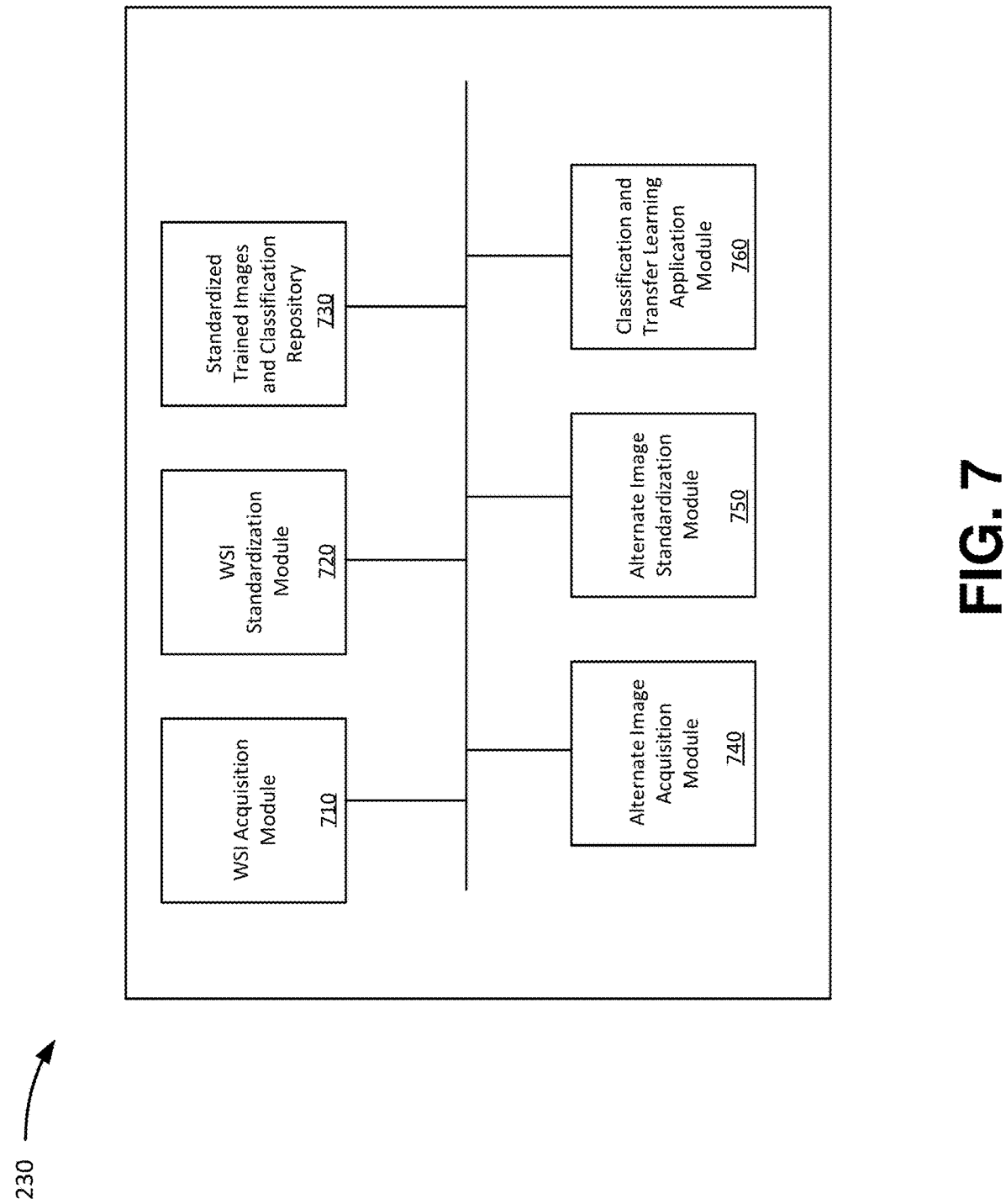
FIG. 7 shows a block diagram of example components of a pathology image training and recognition device in accordance with aspects of the present invention.

FIG. 7 shows a block diagram of example components of a pathology image training and recognition device 230 in accordance with aspects of the present invention. As shown in FIG. 7, the pathology image training and recognition device 230 includes a WSI acquisition module 710, a WSI standardization module 720, a standardized trained images and classification repository 730, an alternate image acquisition module 740, an alternate image standardization module 750, and a classification and transfer learning application protocol module 760. In embodiments, the pathology image training and recognition device 230 includes additional and/or fewer components than those shown in FIG. 7. In embodiments, separate components are integrated into a single computing component or module. Additionally, or alternatively, a single component may be implemented as multiple computing components or modules.

In embodiments, the WSI acquisition module 710 includes a program module (e.g., program module 42 of FIG. 1) that receives WSI training images from the WSI scanner device 210. In embodiments, the WSI acquisition module 710 receives the training images as part of a training process. As described herein, the WSI training images represent images with known classifications/medical diagnoses.

In embodiments, the WSI standardization module 720 includes a program module (e.g., program module 42 of FIG. 1) that standardizes the WSI training images. As described herein, the WSI standardization module 720 standardizes the WSI training images by applying color correction to the WSI training images and blurring the WSI training images to more closely resemble what the WSI training images would look like had they been captured by the alternate image capturing device 220. In embodiments, the WSI standardization module 720 applies color correction by converting the WSI into a hue, saturation, darkness (HSD) color space for separation, classifies pixels in the HSD color space, converts the converted image into a CIELAB (or L*a*b) color space (to standardize the image), and applies a Gaussian filter and blurring. L*a*b color space is a color space defined by the International Commission on Illumination (CIE), and expresses color as three numerical values: L* for lightness, and a* and b* for green-red and blue-yellow color components. Additional details regarding the standardization of the WSI training images are described in greater detail with respect to FIG. 8.

In embodiments, the standardized trained images and classification repository 730 includes a storage system (e.g., storage system 34 of FIG. 1) that stores the known classifications of WSI training image (received as part of the WSI training image from the 710) with identified attributes/patterns of the standardized WSI training image (e.g., generated by the WSI standardization module 720). In embodiments, the standardized trained images and classification repository 730 stores different classifications for different sets of WSI standardized training images. As described herein, information stored by the standardized trained images and classification repository 730 is used as part of transfer learning to evaluate and classify an alternate image (a non-WSI image).

In embodiments, the alternate image acquisition module 740 includes a program module (e.g., program module 42 of FIG. 1) that receives alternate images from the alternate image capturing device 220. In embodiments, the alternate image acquisition module 740 receives the alternate images to classify and evaluate the alternate images (e.g., images of pathological samples).

In embodiments, the alternate image standardization module 750 includes a program module (e.g., program module 42 of FIG. 1) that standardizes an alternate image (e.g., received by the alternate image acquisition module 740). In embodiments, the alternate image standardization module 750 standardizes the alternate image using similar color correcting techniques as those used to standardize the WSI training images (e.g., by the WSI standardization module 720). In this way, the standardized alternate images resemble the standardized WSI images generated by the WSI standardization module 720 and stored in the standardized trained images and classification repository 730.

In embodiments, the classification and transfer learning application protocol module 760 includes a program module (e.g., program module 42 of FIG. 1) that applies trained classifications (e.g. stored by the standardized trained images and classification repository 730) and transfer learning to a standardized alternate image to be evaluated (e.g., generated by the alternate image standardization module 750). By applying the trained classifications and transfer learning, the classification and transfer learning application protocol module 760 classifies the alternate image for image recognition and medical diagnosis.

Figure 8:
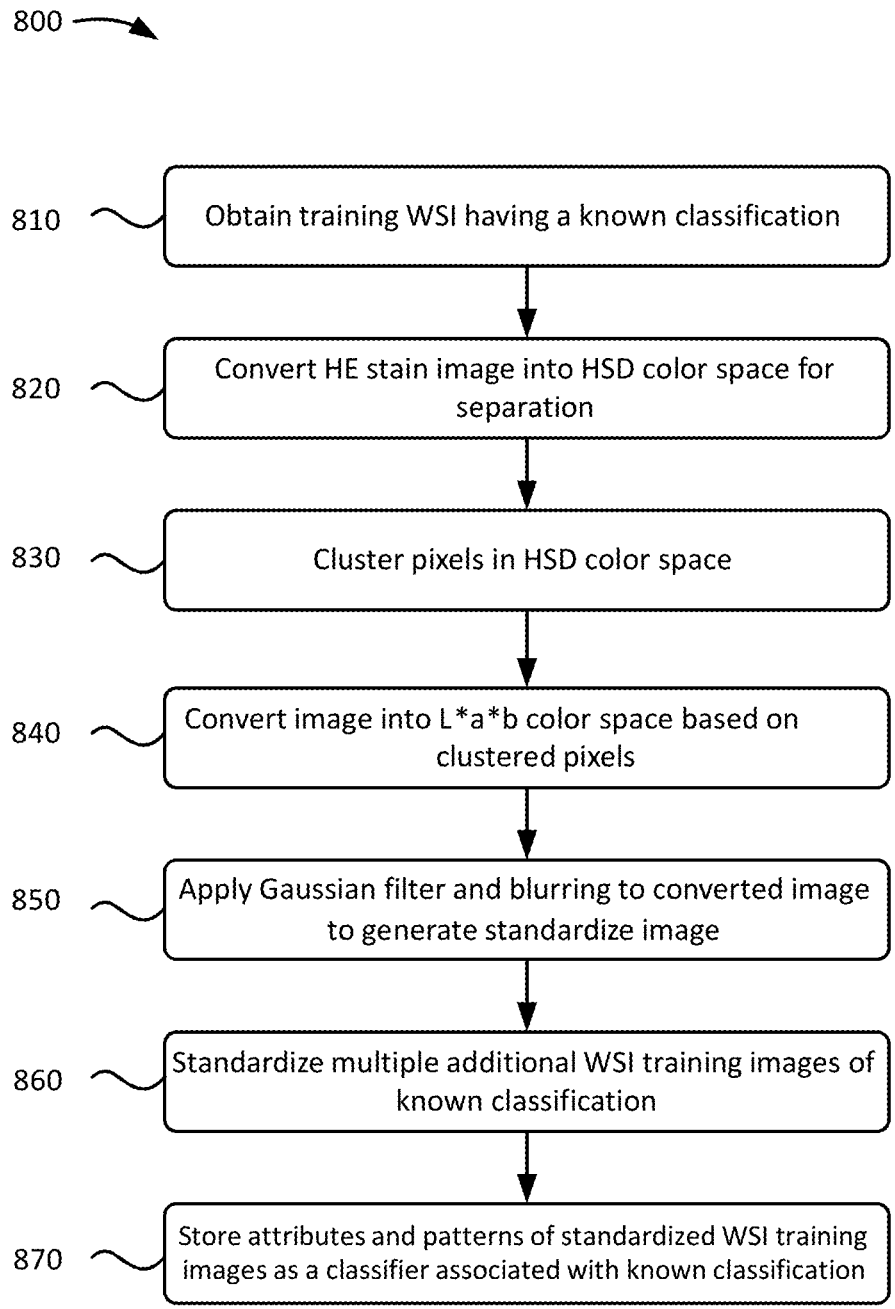
FIG. 8 shows an example flowchart of a process for standardizing WSI training images for generating a classifier to be used to recognize alternate pathology images.

FIG. 8 shows an example flowchart of a process for standardizing WSI training images for generating a classifier to be used to recognize alternate pathology images. The steps of FIG. 8 may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 8, a process 800 includes obtaining a training WSI having a known classification (step 810). For example, as described above with respect to the WSI acquisition module 710, the pathology image training and recognition device 230 obtains a training WSI having a known classification or diagnosis. In an alternative embodiment, the pathology image training and recognition device 230 access a repository having a WSI (e.g., previously produced by the WSI scanner device 210) with a known classification. In embodiments, the WSI includes a hematoxylin and eosin stain (HE stain) or HE stain image.

The process 800 also includes converting the training WSI image (e.g., HE stain image) into an HSD color space for separation (step 820). For example, as described above with respect to the WSI standardization module 720, the pathology image training and recognition device 230 converts the WSI (e.g., the HE stain image) into an HSD color space (e.g., red (R), green (G), and blue (B)) for separation into hematoxylin and eosin portions. In embodiments, the pathology image training and recognition device 230 applies conversion equations to complete the conversion. In an example embodiment, the conversion equations are as follows.

$$(I_R, I_G, I_B) \in [0,255]^3 \quad D = (D_R + D_G + D_B)/3 \quad (1)$$

where $I_R$ is an intensity value for red, $I_G$ is a measure of intensity value for green, $I_B$ is a an intensity value for blue, D is a total density value, $D_R$ is density value for red, $D_G$ is a density value for green, $D_B$ is a density value for blue, and 255 is an incident light value.

$$\begin{cases} D_v = -\ln((I_v+1)/\max(I_v)+2), v \in \{R, G, B\} \\ c_x = \dfrac{D_R}{D} - 1 \\ c_y = (D_G - D_B)/(\sqrt{3} \cdot D) \end{cases} \quad (2)$$

where $D_v$ is a density value, $I_v$ is an intensity value, max( ) is the max intensity value in the image, and $c_x$ and $c_y$ are chromaticity plane which are used to calculate values for H (Hue) and S (Saturation).

Here, max( ) assumes the maximum intensity value of each channel in the image. $D_v$ is a formula derived from Lambert-Beer's law, which is generally given in equation 3. However, since the incident light is not necessarily 255 depending on devices, the maximum value of the image in accordance with aspects of the present invention is approximated to the luminance value of the incident light.

$$D_v = -\ln((I_v+1)/257), v \in \{R,G,B\} \quad (3)$$

where $I_v$ is intensity values which is an RGB color space value (R:0-255, G:0-255, B:0-255) in the image. An RBG color space is any additive color space based on the RGB color model, in which red, green and blue light are added together in various ways to reproduce a broad array of colors. For instance, if the pixel RGB value is (124, 21, 45), then $I_v$=(124, 21, 45). Each density value, $D_R$, $D_G$ and $D_R$ can be calculated from equation 3.

The process 800 further includes clustering pixels in the HSD color space (step 830). For example, as described above with respect to the WSI standardization module 720, the pathology image training and recognition device 230 classifies the pixels in the HSD color space. In embodiments, the pixels in the HSD color space are classified into three classes of background including, for example, hematoxylin, and eosin through Gaussian mixture model (GMM) clustering to determine a posterior probability.

The process 800 also includes converting the image into a L*a*b color space based on the clustered pixels (step 840). For example, as described above with respect to the WSI standardization module 720, the pathology image training and recognition device 230 converts the image (e.g., the WSI training image after HSD color space conversation from step 820 and pixel classification from step 830) into a L*a*b color space. For example, the pathology image training and recognition device 230 performs conversion to an L*a*b color space and the following conversions for the respective pixels to reproduce them in an RGB color space.

$$\begin{bmatrix} l' \\ \alpha' \\ \beta' \end{bmatrix} = \sum_{k=1}^{k} \omega^k \cdot \left( \begin{bmatrix} \dfrac{l^k - \bar{l}^k}{\hat{l}^k} \cdot \sigma_l^k \\ \dfrac{\alpha^k - \bar{\alpha}^k}{\hat{\alpha}^k} \cdot \sigma_\alpha^k \\ \dfrac{\beta^k - \bar{\beta}^k}{\hat{\beta}^k} \cdot \sigma_\beta^k \end{bmatrix} + \begin{bmatrix} \mu_l^k \\ \mu_\alpha^k \\ \mu_\beta^k \end{bmatrix} \right) \quad (4)$$

Here, k ∈{background, hematoxylin, Eosin}; $\omega^k$ is a posterior probability of each k obtained by GMM clustering; $\bar{l}^k \bar{\alpha}^k \bar{\beta}^k$ represents an average value of the respective channels of the image in the k portion in the L*a*b color space; $\hat{l}^k \hat{\alpha}^k \hat{\beta}^k$ represents the standard deviation of the respective channels in the k portion in the L*a*b color space; $\mu_l^k \mu_\alpha^k \mu_\beta^k$ represents the average value of the respective channels of all the learning images in the k portion in the L*a*b color space of WSI; and $\sigma_l^k \sigma_\beta^k \sigma_\alpha^k$ represents the standard deviation of the respective channels of all the learning images in the k portion in the L*a*b color space of WSI.

The process 800 further includes applying a Gaussian filter and blurring to the converted image to generate a standardize image (step 850). For example, as described above with respect to the WSI standardization module 720, the pathology image training and recognition device 230 applies a Gaussian filter and blurring to the converted image (produced by step 840) to generate a standardize image.

As described herein, the process steps 820-850 are substeps for standardizing a WSI training image using the color correction and blurring techniques described herein. However, in one or more alternative embodiments, other color correction and blurring techniques (e.g., in addition to or instead of the techniques described herein) are used to standardize the WSI training image to more closely resemble a pathology image taken by an alternate image capturing device 220.

The process 800 also includes standardizing multiple additional WSI training images of known classifications (step 860). For example, the pathology image training and recognition device 230 repeats the standardization (e.g., process steps 820-850) for additional WSI training images associated with the same known classification as the WSI training image received at step 810. In embodiments, deep machine learning is applied to the group of standardized WSI training images whereby a classifier (e.g., identifying the classification) is configured and associated with the attributes and patterns of the WSI training images.

The process 800 further includes storing attributes and patterns of the standardized WSI training images as a classier associated with the known classification (step 870). For example, the pathology image training and recognition device 230 stores attributes and patterns of the standardized WSI training images (e.g., produced at steps 820-860) and associates a classifier and known classification to those attributes and patterns. As described in greater detail herein, when a pathology image is captured by the alternate image capturing device 220, the pathology image is standardized (e.g., using similar standardization techniques as those use to standardize the WSI training images with the exception of additional blurring). The patterns and attributes (e.g., colors, shapes, curvatures, etc.) of the standardized pathology images captured by the alternate image capturing device 220 are analyzed and transfer learning is implemented to classify the pathology images against the patterns and attributes of the standardized WSI training images.

Figure 9:
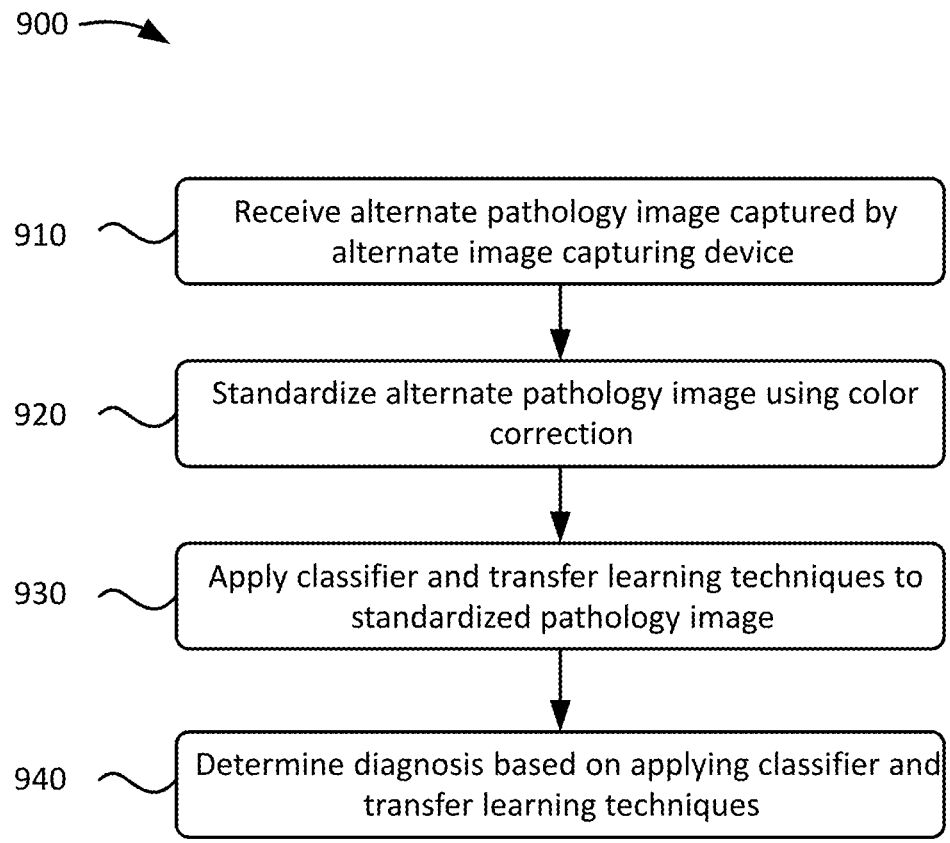
FIG. 9 shows an example flowchart of a process for recognizing and classifying an alternate pathology image captured by an alternate image capturing device.

FIG. 9 shows an example flowchart of a process for recognizing and classifying an alternate pathology image captured by an alternate image capturing device. The steps of FIG. 9 may be implemented in the environment of FIG. 5, for example, and are described using reference numbers of elements depicted in FIG. 5. As noted above, the flowchart illustrates the architecture, functionality, and operation of possible implementations of systems, methods, and computer program products according to various embodiments of the present invention.

As shown in FIG. 9, a process 900 includes receiving an alternate pathology image captured by an alternate image capturing device 220 (step 910). For example, as described above with respect to the alternate image acquisition module 740, the pathology image training and recognition device 230 receives an alternate pathology image captured by the alternate image capturing device 220. In embodiments, the alternate pathology image includes an image to be evaluated and classified (e.g., for medical diagnosis purposes).

The process 900 also includes standardizing the alternate pathology image using color correction (step 920). For example, as described above with respect to the alternate image standardization module 750, the pathology image training and recognition device 230 standardizes the alternate pathology image. In embodiments, the pathology image training and recognition device 230 standardizes the alternate pathology image using similar color correcting techniques as those used to standardize the WSI training images (e.g., by the WSI standardization module 720 and in accordance with the process 800). In embodiments, the pathology image training and recognition device 230 applies color correcting techniques but does not apply blurring filters, as blurring is done to the WSI training images to closer resemble the alternate pathology image.

The process 900 further includes applying a classifier and transfer learning techniques to the standardized pathology image (step 930). For example, as described above with respect to the classification and transfer learning application protocol module 760, the pathology image training and recognition device 230 applies trained classifications (e.g. stored by the standardized trained images and classification repository 730) and transfer learning to a standardized alternate image to be evaluated (e.g., generated by the alternate image standardization module 750). More specifically, the pathology image training and recognition device 230 uses transfer learning to compare the properties and attributes (e.g., colors, shapes, curvatures, patterns, etc.) of the standardized alternate pathology image with the properties and attributes of the standardized WSI trained images.

The process 900 also includes determining a diagnosis based on applying classifiers and transfer learning techniques (step 940). For example, as described above with respect to the classification and transfer learning application protocol module 760, the pathology image training and recognition device 230 determines a diagnosis based on applying classifiers and transfer learning techniques (e.g., from step 930). More specifically, the pathology image training and recognition device 230 compares the properties and attributes of the standardized alternate pathology image with the properties and attributes of the standardized WSI trained images and determines which classification matches the properties and attributes of the standardized alternate pathology image. Based on determining the classification, a corresponding diagnosis is determined. Further, in embodiments, information identifying the classification and diagnosis is output as a report for evaluation by medical professionals by the pathology image training and recognition device 230.

In embodiments, the process 900 is repeated for a group of multiple pathology images from a same sample to analyze the group of images and more accurately classify the sample from the images. As a result of aspects of the present invention, pathology images can be more easily captured by relatively low-cost alternate image capturing devices 220 (in relation to using a WSI scanner device 210) and the pathology images are evaluated with a high degree of accuracy. In this way, it is possible to capture pathology images with a relatively inexpensive alternate image capturing device 220, and accurately recognize the pathology image (e.g., classify and diagnose a medical condition represented by the pathology image). As a result, substantial facility and financial resources are saved, and a greater number of doctors and other medical professionals will be able to leverage pathology classification technology without the need for expensive WSI scanners.

In embodiments, a service provider could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method, via a network. In this case, a computer infrastructure, such as computer system/server 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system/server 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   standardizing a plurality of training pathology images by applying color correction to the plurality of training pathology images, thereby producing standardized training images, wherein the plurality of training pathology images are generated by a first type of device;
   receiving an alternate pathology image captured by a second type of device different than the first type of device;
   standardizing the alternate pathology image by applying, to the alternate pathology image, the color correction applied to the plurality of training pathology images; and
   outputting information regarding a classification of the alternate pathology image to aid in diagnosis of a medical condition represented by the alternate pathology image.

2. The computer-implemented method of claim 1, further comprising determining the classification of the alternate pathology image based on comparing attributes and patterns of the standardized alternate pathology image with attributes and patterns of the standardized training images as identified by a classifier.

3. The computer-implemented method of claim 2, further comprising generating the classifier by applying deep machine learning to the standardized training images.

4. The computer-implemented method of claim 2, wherein an accuracy of the determining the classification of the alternate pathology image is at least 80%.

5. The computer-implemented method of claim 1, wherein:
   the first type of device is a whole slide image (WSI) scanner; and
   the second type of device is not a WSI scanner.

6. The computer-implemented method of claim 5, wherein the standardizing the plurality of training pathology images causes the standardized training images to more closely resemble how the plurality of training pathology images would look if the plurality of training pathology images were captured using the second type of device.

7. A computer program product comprising a computer readable storage medium having program instructions embodied therewith, the program instructions executable by a computing device to cause the computing device to:
   standardize a plurality of training pathology images by applying color correction to the plurality of training pathology images, thereby producing standardized training images, wherein the plurality of training pathology images are generated by a first type of device;
   receive an alternate pathology image captured by a second type of device different than the first type of device;
   standardize the alternate pathology image by applying, to the alternate pathology image, the color correction applied to the plurality of training pathology images; and
   output information regarding a classification of the alternate pathology image to aid in diagnosis of a medical condition represented by the alternate pathology image.

8. The computer program product of claim 7, wherein the program instructions cause the computing device to determine the classification of the alternate pathology image based on comparing attributes and patterns of the standardized alternate pathology image with attributes and patterns of the standardized training images as identified by a classifier.

9. The computer program product of claim 8, wherein the program instructions cause the computing device to generate the classifier by applying deep machine learning to the standardized training images.

10. The computer program product of claim 8, wherein an accuracy of the determining the classification of the alternate pathology image is at least 80%.

11. The computer program product of claim 7, wherein:
    the first type of device is a whole slide image (WSI) scanner; and
    the second type of device is not a WSI scanner.

12. The computer program product of claim 11, wherein the standardizing the plurality of training pathology images causes the standardized training images to more closely resemble how the plurality of training pathology images would look if the plurality of training pathology images were captured using the second type of device.

13. A system comprising:
    a processor, a computer readable storage medium, and program instructions stored on the computer readable storage medium, wherein the program instructions are executable by the processor to cause a computing device to:
    standardize a plurality of training pathology images by applying color correction to the plurality of training pathology images, thereby producing standardized training images, wherein the plurality of training pathology images are generated by a first type of device;
    receive an alternate pathology image captured by a second type of device different than the first type of device;
    standardize the alternate pathology image by applying, to the alternate pathology image, the color correction applied to the plurality of training pathology images; and
    output information regarding a classification of the alternate pathology image to aid in diagnosis of a medical condition represented by the alternate pathology image.

14. The system of claim 13, wherein the program instructions cause the computing device to determine the classification of the alternate pathology image based on comparing attributes and patterns of the standardized alternate pathology image with attributes and patterns of the standardized training images as identified by a classifier.

15. The system of claim 14, wherein the program instructions cause the computing device to generate the classifier by applying deep machine learning to the standardized training images.

16. The system of claim 14, wherein an accuracy of the determining the classification of the alternate pathology image is at least 80%.

17. The system of claim 13, wherein:
the first type of device is a whole slide image (WSI) scanner; and
the second type of device is not a WSI scanner.

18. The system of claim 17, wherein the standardizing the plurality of training pathology images causes the standardized training images to more closely resemble how the plurality of training pathology images would look if the plurality of training pathology images were captured using the second type of device.

19. The system of claim 13, wherein the second type of device is a smartphone.

20. The system of claim 13, wherein the second type of device is mounted to laboratory equipment.

* * * * *